US012622620B2

(12) United States Patent
Linguraru et al.

(10) Patent No.: US 12,622,620 B2
(45) Date of Patent: May 12, 2026

(54) PEDIATRIC HYDRONEPHROSIS SEVERITY FROM ULTRASOUND IMAGES

(71) Applicant: CHILDREN'S NATIONAL MEDICAL CENTER, Washington, DC (US)

(72) Inventors: Marius George Linguraru, Washington, DC (US); Pooneh Roshanitabrizi, Washington, DC (US); Hans G. Pohl, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 411 days.

(21) Appl. No.: 18/554,110

(22) PCT Filed: Apr. 11, 2022

(86) PCT No.: PCT/US2022/024253
§ 371 (c)(1),
(2) Date: Oct. 5, 2023

(87) PCT Pub. No.: WO2022/221187
PCT Pub. Date: Oct. 20, 2022

(65) Prior Publication Data
US 2024/0374189 A1 Nov. 14, 2024

Related U.S. Application Data

(60) Provisional application No. 63/173,755, filed on Apr. 12, 2021.

(51) Int. Cl.
G06K 9/00 (2022.01)
A61B 5/00 (2006.01)
(Continued)

(52) U.S. Cl.
CPC ............ *A61B 5/201* (2013.01); *A61B 5/7246* (2013.01); *A61B 5/7267* (2013.01);
(Continued)

(58) Field of Classification Search
CPC ..... A61B 5/201; A61B 5/7246; A61B 5/7267; A61B 5/7275; A61B 2576/02;
(Continued)

(56) References Cited

U.S. PATENT DOCUMENTS 9,173,590 B2 * 11/2015 Moats .................... A61M 5/007
10,176,575 B2 * 1/2019 Isgum ................... G06T 7/0012
(Continued)

FOREIGN PATENT DOCUMENTS

WO        WO-0057777 A1 * 10/2000    ............. A61B 6/508

OTHER PUBLICATIONS

International Search Report & Written Opinion Issued Aug. 16, 2022, in PCT/US2022/024253, filed on Apr. 11, 2022, 8 pages.

*Primary Examiner* — Shervin K Nakhjavan
(74) *Attorney, Agent, or Firm* — Oblon, McClelland, Maier & Neustadt, L.L.P.

(57) ABSTRACT

A method for predicting a severity and appearance of renal obstruction, including receiving, via processing circuitry, a plurality of medical images corresponding to a kidney of a patient, identifying, the kidney in the plurality of medical images, selecting, at least one relevant image from the plurality of medical images based on a relationship to renal function, standardizing the at least one relevant image, determining, via a deep learning model at least one risk score based on the at least one relevant image, and determining, a final ultrasound-based risk score based on the at least one risk score, wherein the final ultrasound-based risk score is a determination of renal obstruction and/or a probability of renal obstruction. Clinical and/or demographic (Continued)

200

Capturing ultrasound images — 210

Standardizing ultrasound images — 220

Generating risk scores to predict hydronephrosis presence and severity of obstruction using a deep learning-based model — 230

Outputting a final ultrasound-based risk score — 240

Adding related information such as SFU grade, number of selected slices, clinical patient information, and patient demographics — 250

Outputting a final risk score — 260 patient information can be used along with the final ultrasound-based risk score to determine a final risk score to predict the severity and appearance of renal obstruction.

20 Claims, 9 Drawing Sheets

(51) Int. Cl.
  *A61B 5/20* (2006.01)
  *G06T 7/00* (2017.01)
(52) U.S. Cl.
  CPC .......... *A61B 5/7275* (2013.01); *G06T 7/0012* (2013.01); *G06T 2207/10132* (2013.01); *G06T 2207/30084* (2013.01)
(58) Field of Classification Search
  CPC . A61B 2505/01; A61B 5/7253; A61B 5/7282; G06T 7/0012; G06T 2207/10132; G06T 2207/30084
  See application file for complete search history.

(56) References Cited

U.S. PATENT DOCUMENTS

| | | | | |
|---|---|---|---|---|
| 10,699,407 | B2 * | 6/2020 | Isgum .................... | G06N 20/00 |
| 11,864,944 | B2 * | 1/2024 | Fornwalt ............... | G16H 50/20 |
| 2005/0058598 | A1 * | 3/2005 | Degani .................. | A61K 49/06 |
| | | | | 424/9.3 |
| 2013/0184584 | A1 * | 7/2013 | Berkey ............... | A61B 8/5292 |
| | | | | 600/441 |
| 2016/0018412 | A1 | 1/2016 | Anderberg et al. | |
| 2018/0333140 | A1 | 11/2018 | Wodlinger et al. | |
| 2020/0034970 | A1 | 1/2020 | Linguraru et al. | |
| 2020/0395129 | A1 * | 12/2020 | Kalkstein ............... | G16H 50/70 |
| 2024/0428417 | A1 * | 12/2024 | Chen .................... | G06T 7/0016 |

* cited by examiner

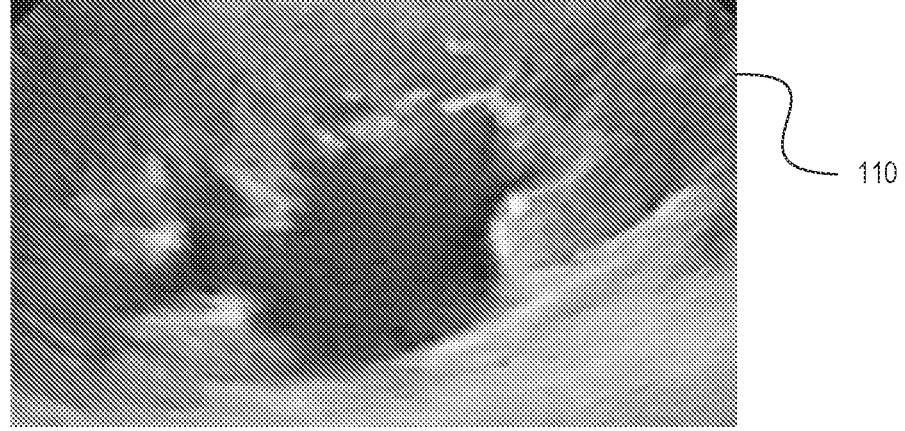
110
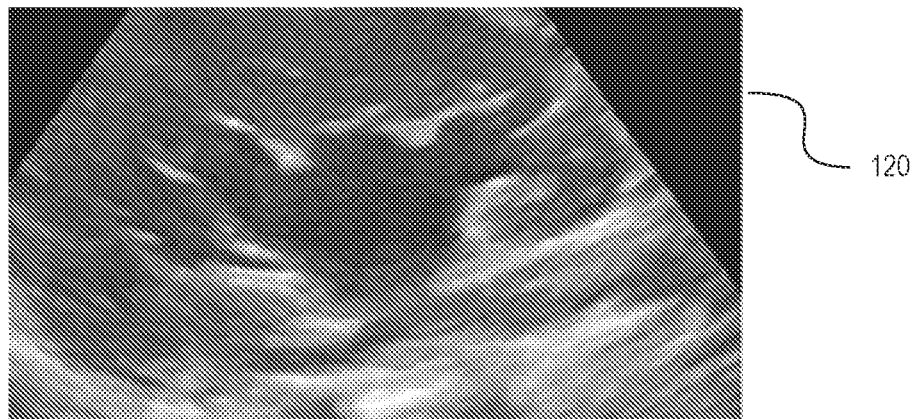
120
*FIG. 1*

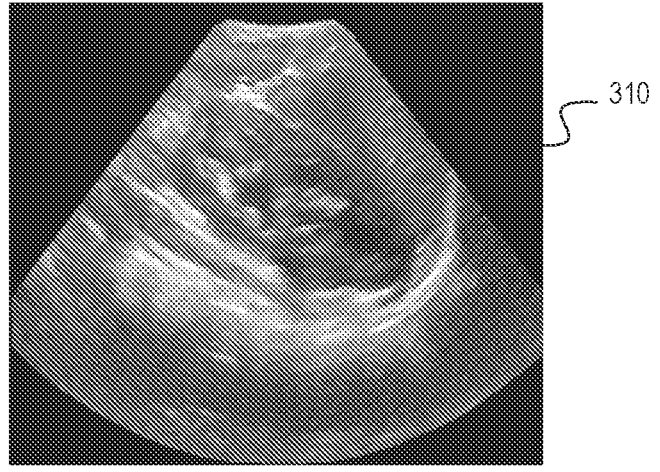
310
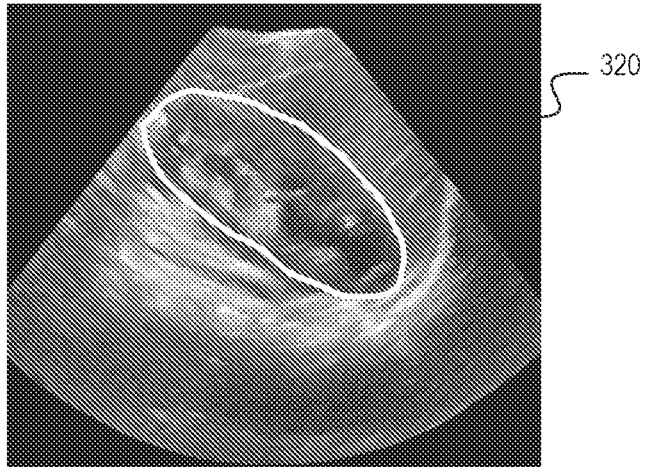
320
*FIG. 3*

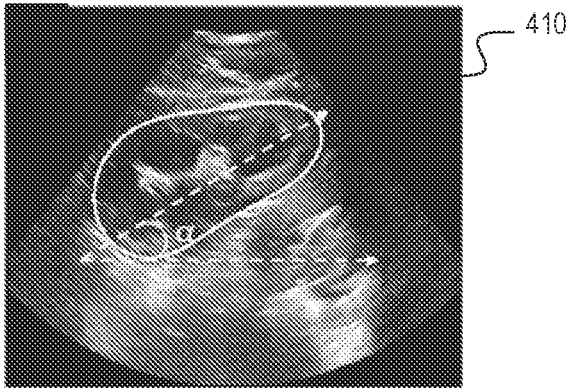
410
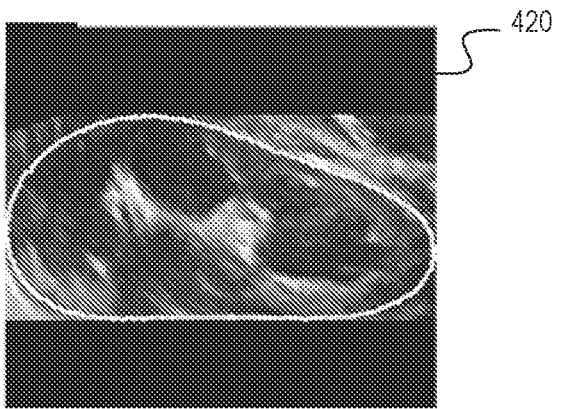
420
*FIG. 4*

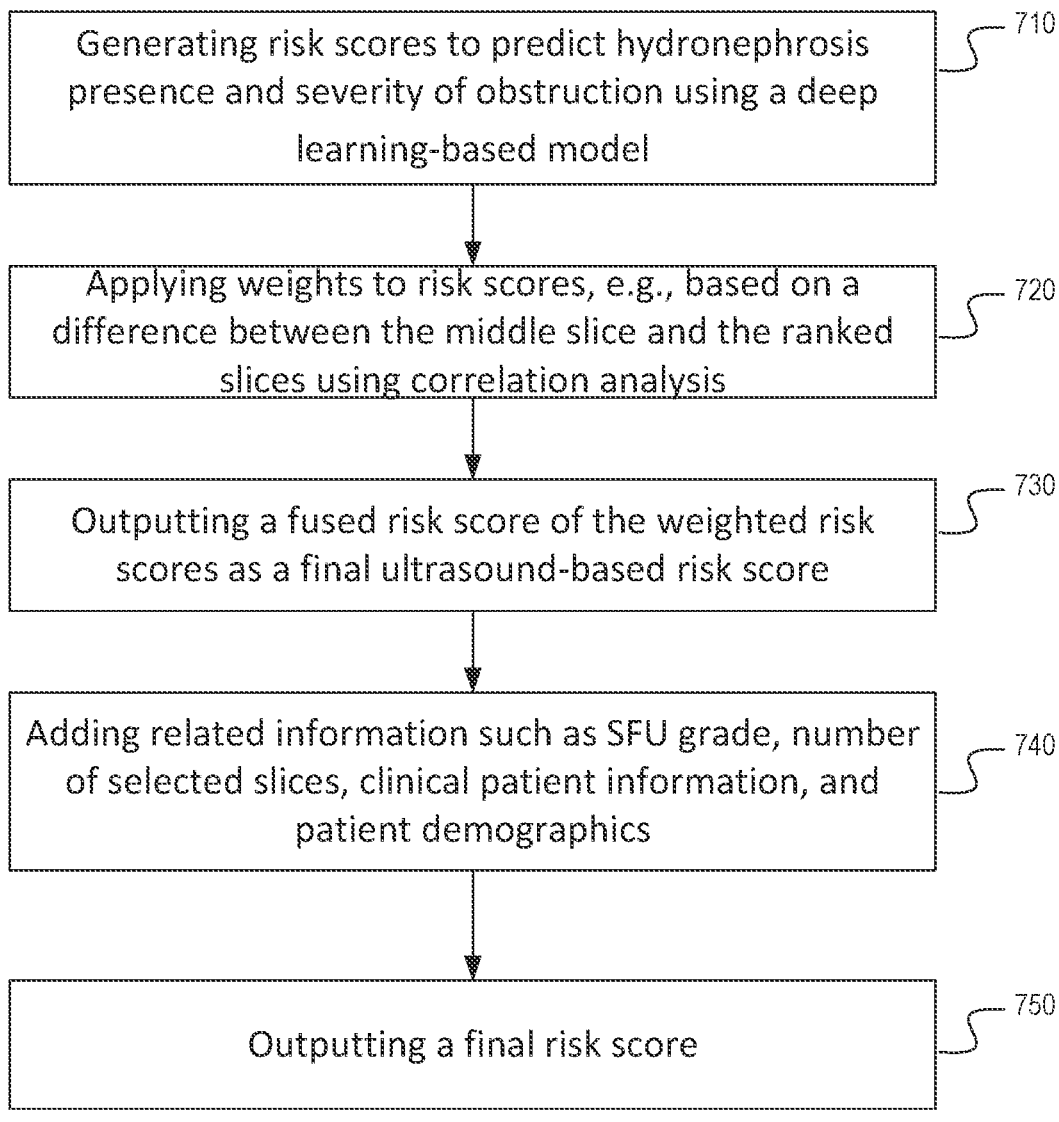

700

Generating risk scores to predict hydronephrosis presence and severity of obstruction using a deep learning-based model — 710

Applying weights to risk scores, e.g., based on a difference between the middle slice and the ranked slices using correlation analysis — 720

Outputting a fused risk score of the weighted risk scores as a final ultrasound-based risk score — 730

Adding related information such as SFU grade, number of selected slices, clinical patient information, and patient demographics — 740

Outputting a final risk score — 750

FIG. 7

PEDIATRIC HYDRONEPHROSIS SEVERITY FROM ULTRASOUND IMAGES

CROSS-REFERENCE TO RELATED APPLICATIONS

The present application claims priority to U.S. Provisional Application No. 63/173,755, filed Apr. 12, 2021, which is incorporated herein by reference in its entirety for all purposes.

BACKGROUND

Field of the Disclosure

The present disclosure is generally directed to systems, methods, and apparatuses for predicting kidney function. More specifically, embodiments of the present disclosure involve systems, methods, and apparatuses for assessing renal obstruction, including identification of a presence of renal obstruction and determination of a severity or a likely severity of renal obstruction.

Description of the Related Art

Hydronephrosis is a dilatation of the renal collecting system resulting from a buildup of fluid that cannot be drained from the kidney. Congenital hydronephrosis is common in children and is typically evaluated using visual assessment of ultrasound images. For example, the Society for Fetal Urology (SFU) has developed a grading system to visually assess hydronephrosis severity using ultrasound images. However, the grading system has been shown to lack apparent correlation with other functional imaging modalities that provide information about renal function. Renal obstruction, such as at ureteropelvic junction, can cause hydronephrosis. Untreated obstruction can result in permanent loss of kidney function. Variability in ultrasound images, especially for pathological kidneys, can result in difficulty determining renal obstruction and dysfunction using ultrasound. In addition, visual assessment of ultrasound images is a subjective process that usually requires expert interaction. As a result, the presence and severity of renal obstruction is typically evaluated using more invasive techniques such as diuresis renography. Diuresis renography is costly and can require sedation in children, while ultrasound imaging is comparatively quicker and used as a routine procedure.

The foregoing Background description is for the purpose of generally presenting the context of the disclosure. Work of the inventors, to the extent it is described in this background section, as well as aspects of the description which may not otherwise qualify as prior art at the time of the filing, are neither expressly or impliedly admitted as prior art against the present disclosure.

SUMMARY

According to one embodiment, the present disclosure relates to a method for predicting a severity and appearance of renal obstruction, including receiving, via processing circuitry, a plurality of medical images corresponding to a kidney of a patient, identifying, via the processing circuitry, the kidney in the plurality of medical images, selecting, via the processing circuitry, at least one relevant image from the plurality of medical images, the at least one relevant image being selected based on a relationship to renal function, standardizing, via the processing circuitry, the at least one relevant image, determining, via a deep learning model executed by the processing circuitry, at least one risk score based on the at least one relevant image, and determining, via the processing circuitry, a final ultrasound-based risk score based on the at least one risk score, wherein the final ultrasound-based risk score is a determination of renal obstruction and/or a probability of renal obstruction.

According to another embodiment, the present disclosure relates to an apparatus for predicting a severity and appearance of renal obstruction, including processing circuitry configured to receive a plurality of medical images corresponding to a kidney of a patient, identify the kidney in the plurality of medical images, select at least one relevant image from the plurality of medical images, the at least one relevant image being selected based on a relationship to renal function, standardize the at least one relevant image, determine, via a deep learning model, at least one risk score based on the at least one relevant image, and determine a final ultrasound-based risk score based on the at least one risk score, wherein the final ultrasound-based risk score is a determination of renal obstruction and/or a probability of renal obstruction.

According to another embodiment, the present disclosure relates to a non-transitory computer-readable storage medium for storing computer-readable instructions that, when executed by a computer, cause the computer to perform a method for predicting a severity and appearance of renal obstruction, the method including receiving, via processing circuitry, a plurality of medical images corresponding to a kidney of a patient, identifying, via the processing circuitry, the kidney in the plurality of medical images, selecting, via the processing circuitry, at least one relevant image from the plurality of medical images, the at least one relevant image being selected based on a relationship to renal function, standardizing, via the processing circuitry, the at least one relevant image, determining, via a deep learning model executed by the processing circuitry, at least one risk score based on the at least one relevant image, and determining, via the processing circuitry, a final ultrasound-based risk score based on the at least one risk score, wherein the final ultrasound-based risk score is a determination of renal obstruction and/or a probability of renal obstruction.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 illustrates ultrasound images, according to one embodiment of the present invention;

FIG. 3 illustrates a segmented ultrasound image, according to one embodiment of the present invention;

FIG. 4 illustrates a standardized field of view for an ultrasound image, according to one embodiment of the present invention;

FIG. 7 illustrates a method for determining a final risk score, according to one embodiment of the present invention.

DETAILED DESCRIPTION

Figure 2A:
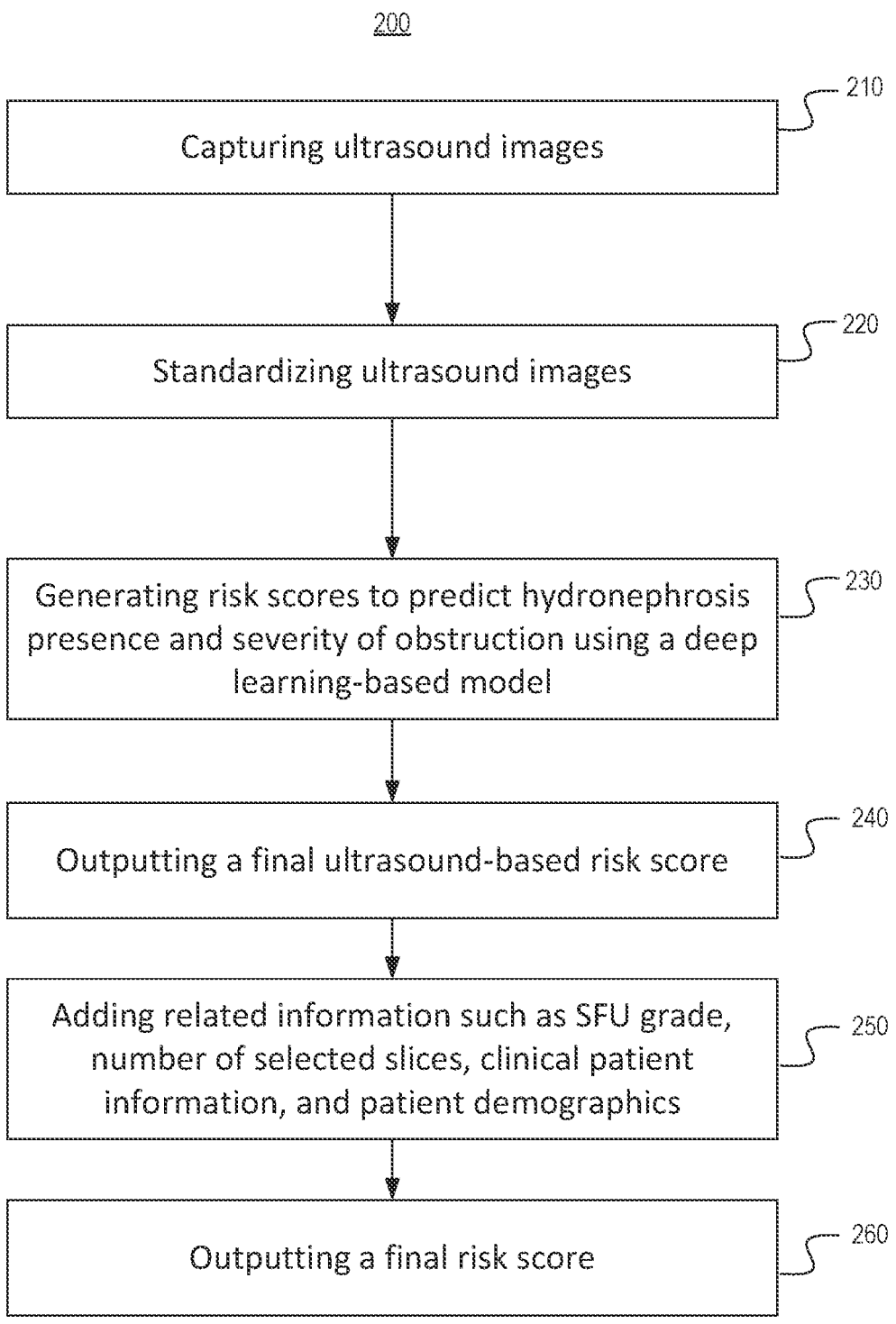
FIG. 2A illustrates a method for obtaining a final risk score, according to one embodiment of the present invention.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as "comprising" (i.e., open language). Reference throughout this document to "one embodiment," "certain embodiments," "an embodiment," "an implementation," "an example," or similar terms means that a particular feature, structure, or characteristic described in connection with the embodiment is included in at least one embodiment of the present disclosure. Thus, the appearances of such phrases in various places throughout this specification are not necessarily all referring to the same embodiment. Furthermore, the particular features, structures, or characteristics may be combined in any suitable manner in one or more embodiments without limitation.

According to one embodiment, the present approach is directed to detecting a presence and/or severity of renal obstruction using ultrasound images. Specifically, the present invention aims to improve clinical interpretation of ultrasound images to accurately predict presence and severity of renal obstruction as a cause of pediatric hydronephrosis. Ultrasound imaging is non-invasive and cost-effective compared to other renal procedures, such as diuresis renography. However, classifying hydronephrosis using ultrasound images often requires a high amount of expert user interaction to segment and prepare images and/or to analyze the images. Pathological kidneys, such as kidneys with dilatation, are especially difficult to segment, as textures and boundaries of renal ultrasound images are not uniform or homogenous. Current standards and indices for clinical detection of hydronephrosis using ultrasound images correlate poorly with actual kidney function, resulting in further procedures for patients with suspected moderate or severe hydronephrosis. In one embodiment, the present invention presents a deep learning-based approach for directly predicting renal obstruction presence and severity using ultrasound images in order to accurately detect and classify pediatric hydronephrosis. The present approach is differentiated from previous methods in that the present approach can automate segmentation and standardization of ultrasound images, which minimizes or eliminates user interaction and enables accurate assessment of the ultrasound images by a deep learning-based model. Additionally, the present approach can directly predict obstruction and hydronephrosis severity using a model that is correlated with metrics of kidney function.

In one embodiment, the present approach can include predicting a presence and severity of renal obstruction using an ultrasound-based risk score. In one embodiment, the present approach can also incorporate multiple sources of information in addition to ultrasound image assessment to improve the prediction of presence and severity of renal obstruction. For example, alternative metrics or models for grading ultrasound images can be used to enhance the overall predictive power of the present approach. In one embodiment, clinical patient information can be used to enhance the overall predictive power of the model. Clinical patient information can include, but is not limited to, demographic information, medical history, and results of other clinical assessments, as will be discussed in greater detail elsewhere in this disclosure. In one embodiment, clinical patient information can include an indication of dilation size of the collecting system. In one embodiment, the final prediction of a presence and/or severity of renal obstruction can be a final risk score. The final risk score can be evaluated using a classifier, as will be discussed in greater detail elsewhere in this disclosure.

Diuresis renography is an imaging procedure for evaluating the relative function/contribution of each kidney and the capacity of a renal system for handling a bolus of urine. The washout or drainage half-time (T½) in diuresis renography is the time it takes for half of an injected radiotracer to drain after reaching a peak amount in the kidney. T½ is a useful metric for assessing renal obstruction. However, current methods for assessing hydronephrosis using ultrasound images, such as the SFU grading system, correlate poorly with T½ values obtained from diuresis renography. For example, FIG. 1 illustrates two ultrasound images of kidneys with apparent hydronephrosis. The ultrasound images of the first kidney 110 and the second kidney 120 are both given the same grade using the visual assessment of the SFU grading system. However, the first kidney 110 has a T½ value of 69 minutes, which is indicative of obstruction in the kidney, while the second kidney 120 has a T½ value of 3 minutes, which suggests the kidney is not obstructed. The difference in T½ values between the first kidney 110 and the second kidney 120 shows that the SFU grading system is not a reliable metric for assessing obstruction and kidney function. Therefore, systems and methods that utilize the SFU grading system for hydronephrosis analysis will not be able to accurately predict obstruction using ultrasound images alone. In one embodiment, the present approach does not rely on the SFU grading system but rather can predict obstruction severity using a risk metric that correlates with T½ values, leading to more accurate assessment of kidney function. In another embodiment, the present approach can predict obstruction severity using a risk metric that correlates with alternative measures of renal function, including, but not limited to, kidney drainage (e.g., C30, or clearance at 30 minutes), kidney clearance (e.g., CUP, or clearance upright, a percentage of residual tracer cleared in the upright position), and/or differential renal function. In one embodiment, the present approach can be used to predict a clinical outcome, including, but not limited to, surgical procedure, discharge from a hospital, and longitudinal follow-up recommendations.

In one embodiment, the present invention can include a deep learning-based approach to analyzing ultrasound images. FIG. 2A illustrates a computer-based method 200 for analyzing ultrasound images according to one embodiment of the present invention. Ultrasound images can be collected in step 210. In one embodiment, a manual sweep can be used to collect the ultrasound images. In another embodiment, volumetric acquisition can be used to collect the ultrasound images. After an ultrasound is performed in step 210, the collected set of ultrasound images can be standardized in step 220. In one embodiment, standardization of the ultrasound images can include identifying the kidney in the ultrasound images, extracting relevant images from the ultrasound images, and standardizing a field of view of the images. Identifying the kidney can include segmenting the kidney region manually, semi-automatically, or automatically. The relevant images can be selected based on the visible components of the kidney. The relevant images can include, for example, certain regions of the kidney, such as the renal pelvis and calyces. In one embodiment, the relevant images can include a middle slice image and adjacent slice images. The relevant images can then be analyzed in step 230 by a deep learning-based model to predict presence and severity of obstruction. The prediction of the presence and severity of obstruction can be quantified by a risk score. A final ultrasound-based risk score can be outputted in step 240 based on the individual risk scores of the most relevant images. In one embodiment, the final ultrasound-based risk score can be a binary label of the kidney as obstructed or not obstructed. In another embodiment, the final ultrasound-based risk score can be a probability of a presence and/or a severity of obstruction. The final ultrasound-based risk score can be enhanced with additional information related to the patient. Additional information such as an SFU grade, a number of selected slices, clinical parameters, and/or patient demographics can be incorporated in addition to the final ultrasound-based risk score in step 250 to improve prediction accuracy. The additional information can be used to output a final risk score in step 260. In one embodiment, the final risk score can be a probability of renal obstruction, such as obstruction at the junction of the kidney and the ureter. In one embodiment, the final risk score can be used to predict hydronephrosis severity as a result of obstruction. In another embodiment, the final risk score can be a binary label of the kidney as obstructed or not obstructed. The final ultrasound-based risk score and/or the final risk score can be assessed using a classifier.

Visual assessment of ultrasound images has typically been a subjective process that requires expert opinion and user interaction. Procedural variability, such as differences in probe orientation and patient positioning, results in variability in ultrasound images. In addition, renal defects such as hydronephrosis can affect the appearance of the kidney, requiring a trained professional to properly distinguish and assess ultrasound images. Automated methods for analyzing renal ultrasound images often depend on heavy user interaction for parameter initialization and image selection in order to identify and segment the kidney. There is therefore a need for an automated process that can standardize ultrasound images to reduce non-discriminative variability between image datasets acquired during routine clinical evaluations.

Figure 2B:
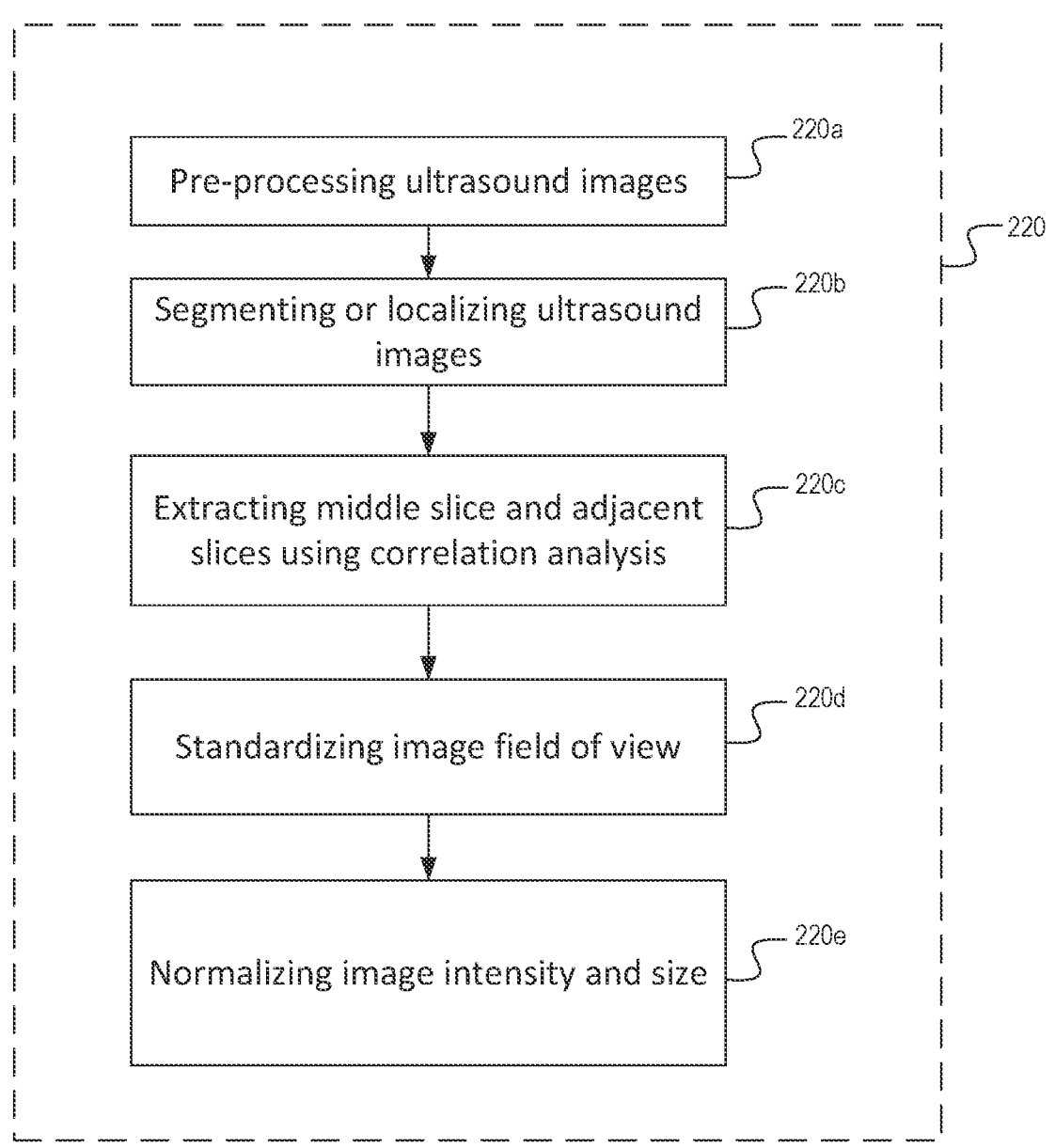
FIG. 2B illustrates a sub-method for standardizing ultrasound images, according to one embodiment of the present invention.

FIG. 2B is a flow chart of a method 220 for standardizing ultrasound images according to one embodiment of the present invention.

In one embodiment, the ultrasound image can be modified before segmentation in a pre-processing step 220*a*. For example, the size of the ultrasound image can be standardized (e.g., to 256 pixels by 256 pixels). In one embodiment, the image can be padded with zeros or resampled to meet a standard size requirement. In one embodiment, the ultrasound image can be resampled to a uniform voxel size (e.g., 0.28 mm×0.22 mm×0.44 mm).

Segmentation or boundary localization in step 220*b* is the process of identifying the kidney in the ultrasound image and determining the boundaries of the kidney. The kidney can be segmented manually, semi-automatically, or automatically. In one embodiment, the boundaries of the kidney can be localized, e.g., in an oriented bounding box. In one embodiment, the boundary can be localized using a convolutional neural network.

In one embodiment, the present invention can include at least one segmenting neural network (NN) for segmenting the kidney in the ultrasound image, e.g., a LinkNet neural network, a U-net neural network. In one embodiment, the at least one segmenting NN can be trained, e.g., using a Dice loss function. The Dice coefficient is a measure of similarity and can be used to compare a predicted value and an actual value. For example, the Dice coefficient can be calculated based on predicted and actual boundary pixels in an image. Minimizing Dice loss (1–Dice coefficient) can increase a model's accuracy by maximizing overlap between a model's predicted set of values and an actual set of values. Minimizing Dice loss can be especially effective for image segmentation with thin boundaries. In one embodiment, the Dice loss can be minimized using the Adam optimization algorithm and an adaptive learning rate. For example, an adaptive learning rate $l_r$ can be modeled by $l_r$=(Unit(epoch–50)×$10^{-4}$×$e^{-0.1}$)+(Unit(50–epoch)×$10^{-4}$, with 100 epochs. The Heaviside step function can be used as the Unit function. In one embodiment, the at least one segmenting NN can be trained, e.g., using a batch size of 8.

In one embodiment, the at least one segmenting NN can be trained using a cross-entropy loss function. In one embodiment, the at least one segmenting NN can be trained using stochastic gradient descent with momentum. In one embodiment, the at least one segmenting NN can include a pretrained encoder, e.g., a VGG16 neural network as an encoder. A 1×1 convolution filter can be used to modify the dimensions of an input into the encoder. In one embodiment, the at least one segmenting NN can include a nested structure. The nested structure can include skip connections between the encoding and the decoding path.

In one embodiment, the at least one segmenting NN can be a convolutional neural network (CNN). The convolutional kernel used by the at least one segmenting CNN can be a representation of an expected appearance of a kidney in an ultrasound image. In one embodiment, the convolutional kernel can be developed by the at least one segmenting CNN using reference ultrasound images. For example, the at least one segmenting NN can be trained on positive examples of a kidney in an ultrasound image and negative examples of a background or surrounding area. The at least one segmenting CNN can then determine a kernel that corresponds to the kidney in the ultrasound image based on the positive and negative examples.

In one embodiment, the at least one segmenting NN can be a CNN including two convolutional layers followed by two max pooling layers and two fully connected layers. The convolutional layers can use a kernel to process the input image and return an output matrix. The kernel can be transformed, e.g., the orientation and/or the scale of the kernel can be modified for each convolution. The max pooling layers can take the maximum values of pools (portions) of the output matrix of the convolutional layers in order to reduce the size of the output matrix and extract representative features. In one embodiment, average pooling can be used in place of or in addition to max pooling. The pooled output matrix of the pooling layers can then be used as an input into the fully connected layers. In one embodiment, the fully connected layers can use a network of fully connected neurons to classify the images as represented by the pooled output matrix.

In one embodiment, a rectified linear unit (ReLU) activation function can be applied after each layer except the last layer of the at least one segmenting NN. The ReLU function can eliminate negative values so that only positive values are input into the next layer. In one embodiment, a softmax function can be used to normalize the output of the last layer to a probability distribution such that the output can be interpreted as a probability. The softmax function applies an exponential function to map an input vector of real numbers to an output vector of probabilities between 0 and 1. In one embodiment, the last fully connected layer can be followed by a dropout layer. The dropout layer can eliminate units, connections, and/or weights in the neural network to reduce overfitting to training data, which can result in the network being too rigid. The keep rate of the dropout layer is the frequency at which units are eliminated. In one embodiment, multiple neural networks can be used to segment the image. For example, a different neural network can be used to determine the position, orientation, or size of the kidney for segmentation.

In one embodiment, a bounding box can be drawn around the kidney based on the output of the at least one segmenting NN. In one embodiment, the bounding box can be generated based on a maximum probability determined by the at least one segmenting NN. In one embodiment, a classifier (e.g., a support vector machine (SVM)) can be used to assess the convolution results. For example, the bounding box can be generated based on a distance between the convolution results and a classifying function or plane of the classifier.

In one embodiment, a real time template deformation algorithm can be used to identify the boundaries of the kidney in the ultrasound image for segmentation. A template boundary is aligned to a region of interest, e.g., the kidney, in the image. The likelihood of intensity distributions inside and outside of the template boundary can be used to determine a similarity between the template and the region of interest. In one embodiment, edge detection can be used to align the template with the region of interest. In one embodiment, threshold values can be used to determine whether the template matches the region of interest. The threshold values can be adjusted based on each image. The template deformation algorithm can be applied to segment the image automatically.

In one embodiment, the template deformation algorithm can accept user input to adjust or deform a template in real time. For example, the user input can include identification of points known to be inside or outside of the kidney. The identified points can then be used as constraints on the deformation function. The constraints can be used as anchor points to determine the boundary of the model and correct the direction of the deformable model with respect to the kidney boundary. User input is useful, for example, to improve matching and segmentation in images with high noise, shadows, and/or partial kidney occlusion. In one embodiment, the user input can be an indication on a display, e.g., a touch screen display. In one embodiment, the user input can be at least one coordinate, e.g., a pixel coordinate. In one embodiment, the user input can be an area, a segment, or a feature of the ultrasound image along with a classification of the area, segment, or feature. For example, the user input can be a selection of a center of the kidney or an area inside the kidney. In one embodiment, user input can be used to confirm the segmented image. In one embodiment, clinical patient information, including, but not limited to, demographic information, can also be used to identify the kidney in the ultrasound image. The clinical patient information can be a user input.

In one embodiment, a probabilistic atlas can be used to emphasize a probable kidney region in the ultrasound image. The atlas can include images and/or composite images from a plurality of kidney slices. In one embodiment, a statistical shape model (SSM) can be used to refine the segmented image based on the probabilistic atlas. In one embodiment, the SSM can be implemented by reorienting the segmented image to correct pose parameters and remove translation. Reorienting the segmented image can include reorienting the image along the longest axis in a coronal view and around center contour points in the image. In one embodiment, uniform samples along the kidney contours between major landmarks along the main axes of the kidney can be taken to assess the kidney segmentation. In one embodiment, an affine transform can be applied to the probabilistic atlas based on the major landmarks.

The step of segmenting the image can be repeated for a plurality of slices from the ultrasound image. Each slice is an image that captures a view of the kidney based on the probe position during the ultrasound. However, certain slices may contain redundant or less relevant information about the kidney and related areas of interest. Identifying and extracting images that contain relevant information can improve prediction accuracy and efficiency. In one embodiment, the relevant images can include visual information related to renal function. For example, the relevant images can include a full coronal view of the renal pelvis and calyces, which are areas where obstruction can occur. In one embodiment, as in step 220c of FIG. 2B, the relevant images can include a middle slice and adjacent slices. In one embodiment, the middle slice of the kidney can be an image of a segmented renal capsule with a maximum cross-sectional area in a coronal view. The cross-sectional area can be calculated as, for example, a number of pixels within the segmented renal capsule. The maximum cross-sectional area can provide the most information about dilatation and corresponding renal function.

In one embodiment, additional images of adjacent slices to the middle slice can also be extracted as relevant images and used for analysis. The adjacent slices can be identified based on correlation analysis between each slice and the middle slice. For example, a Pearson correlation coefficient between each slice and the middle slice can be calculated. A slice can be considered adjacent if the correlation coefficient between the slice and the middle slice is greater than a threshold value, e.g., the correlation coefficient can be greater than or equal to 0.83. In one embodiment, an alternative measure of linear correlation between each slice and the middle slice can be used to select the adjacent slices. The middle slice and the adjacent slices can include the anatomical regions most relevant to the assessment of hydronephrosis. The adjacent slices can also provide 3D image information for a more comprehensive analysis of renal appearance and morphology. In one embodiment, core areas of the kidney in the middle and adjacent slices can be identified using correlation analysis. Core areas can include, for example, the pelvis and calyces. Correlation values between slices can indicate that an adjacent slice contains the core areas.

The field of view of the middle slice and the adjacent slices can be standardized in step 220d. Standardization of the field of view can include aligning the middle and adjacent slices to improve assessment of obstruction by a deep learning-based model. Standardization of the field of view can result in anatomical regions in the kidney being approximately aligned for each slice. Standardizing the field of view of each slice can also improve the automated prediction of obstruction using a plurality of images. For example, the same kernels and/or templates can be applied to the images by a deep learning-based model without the need to match the orientation of the kernels to each image.

In one embodiment, the images of the kidney such as the middle slice and the adjacent slices can be further standardized to improve analysis, as in step 220e. For example, pixel values inside the kidney region in each image can be normalized, e.g., scaled to a range of [0, 1]. In one embodiment, the intensity of each image can be standardized. In one embodiment, the images can be padded with zeros to standardize the sizes of the images, e.g., to 256×256 pixels.

It can be recognized that the order of the steps described in the method of FIG. 2B for standardizing ultrasound images can be modified to achieve the same result of standardization. In one embodiment, the middle slice and the adjacent slices can be identified and extracted as in step 220c before the field of view of each slice is standardized as in step 220d. This sequence reduces the number of images that must be corrected for field of view. In another embodiment, the field of view for each slice is standardized as in step 220d before the middle slice and the adjacent slices are selected as in step 220c. Standardizing the field of view for each slice can make identification of the middle slice and the adjacent slices more efficient. Both sequences are compatible with the present invention.

FIG. 3 illustrates segmented and standardized ultrasound images according to one embodiment of the present invention. An ultrasound image 310 includes the kidney as well as background image data. A convolutional neural network and template deformation algorithm as described above can be used to identify the boundaries of the kidney to produce a segmented image 320. In one embodiment, the segmented image 320 can be a middle slice image. This process can be performed for a series of slices captured during a single procedure.

FIG. 4 illustrates an example of standardization of the field of view of an ultrasound image according to one embodiment of the present invention. In one embodiment, the orientation of the slices can be standardized along the longest axis in the coronal view. The longest axis of the kidney can be identified and highlighted as in pre-rotation image 410. The longest axis is the axis along which the longest line segment that spans the segmented kidney can be drawn. The kidney can then be rotated an angle α such that the longest axis is horizontal as in the standardized image 420. The identification of the longest axis and the image rotation can be repeated for a middle slice and for adjacent slices. The angle α can be different for each slice depending on the positioning of the respective longest axes.

After the kidney images have been segmented and standardized, a deep learning prediction model can be used to predict a severity of kidney obstruction based on the middle slice and the adjacent slices. According to one embodiment, the prediction model can be trained on reference ultrasound images. In one embodiment, the reference ultrasound images can include ultrasound images with geometric augmentations, including, but not limited to, vertical flips, rotations (e.g., between −10° and 10°), and translations (e.g., between −2 mm and 2 mm). According to an example embodiment, the prediction model can be trained using a binary cross-entropy loss function. In one embodiment, the prediction model can be trained using stochastic gradient descent with momentum. In one embodiment, for example, a batch size of 4 and 100 epochs can be used for an Adam optimization algorithm with learning rate $l_r = (\text{Unit}(\text{epoch}-50) \times 10^{-4} \times e^{-0.1}) + (\text{Unit}(50-\text{epoch}) \times 10^{-4}$. The Heaviside function can be used as the Un function. The parameters and training of the prediction model can be adjusted to provide the best performance (e.g., most accurate prediction) for a population, a sample, or a dataset.

Figure 5:
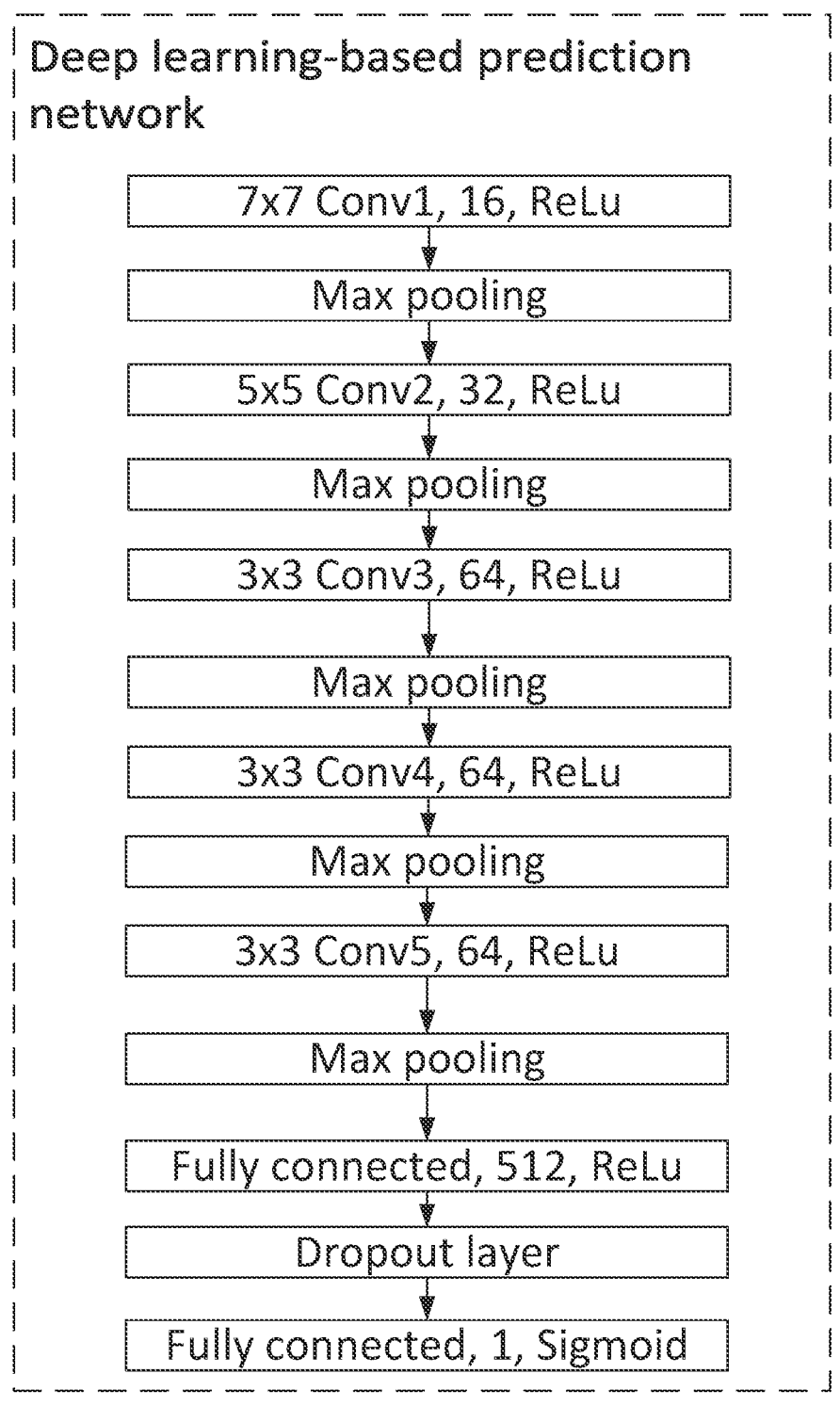
FIG. 5 illustrates a deep learning-based prediction model, according to one embodiment of the present invention.

FIG. 5 illustrates an example architecture of a deep learning prediction model that can be used to predict the severity of hydronephrosis according to one embodiment of the present invention. The input to the model can be a standardized and segmented kidney image such as a middle slice image or an adjacent slice image. In one embodiment, the model can include five convolutional layers, a fully connected layer of 512 units, and a final output layer of 1 unit. In one embodiment, the first convolutional layer can include 16 filters and can use an input patch of 7×7 pixels. The input patch is a portion of the input image used for each convolution operation. In one embodiment, the second convolutional layer can include 32 filters and can use an input patch of 5×5 pixels. The remaining convolutional layers can each include 64 filters and use an input patch of 3×3 pixels. As a non-limiting example, a stride length of 2×2 pixels can be used for convolution. In one embodiment, each layer excluding the final output layer can use a ReLU activation function to eliminate nonpositive inputs.

In one embodiment, max pooling (e.g., 3×3 max pooling) can be used to down sample the output of at least one layer in the deep learning-based network. For example, max pooling can be used to pool the output matrix of each convolutional layer. In one embodiment, the max pooling can be done using a stride length, e.g., a stride length of 2, in each dimension. In one embodiment, batch normalization can be used to stabilize the model and normalize the output of at least one layer to a probability distribution. The normalized output can then be used as an input to the next layer. The final output layer of the network can include a filter. In one embodiment, the network can include a dropout layer after the first fully connected layer. The keep rate of the dropout layer can be selected based on empirical data to reduce overfitting. For example, the dropout layer can have a keep rate, e.g., of 0.3. While the architecture described in the foregoing embodiment has demonstrated great success in a variety of uses and applications, it can be appreciated that alternative structures and deep learning-based models for predicting presence and severity of obstruction can also be compatible with the present invention.

In one embodiment, the output of the prediction model can be a classification of the image. The classification can be, for example, the presence or absence of renal obstruction. In one embodiment, the classification can be based on whether the predicted renal capsule meets a level of obstruction. The level of severity and obstruction can be defined by a metric of renal function, such as T½. In one embodiment, the final fully connected layer can apply a function, e.g., a sigmoid probability function to transform a classification output to a probability of renal obstruction. The probability of renal obstruction can be used as a risk score to assess presence and severity of obstruction. Parameters of the sigmoid, such as the dynamic range, symmetry, and slope, can be adjusted to increase accuracy of the output.

Figure 6:
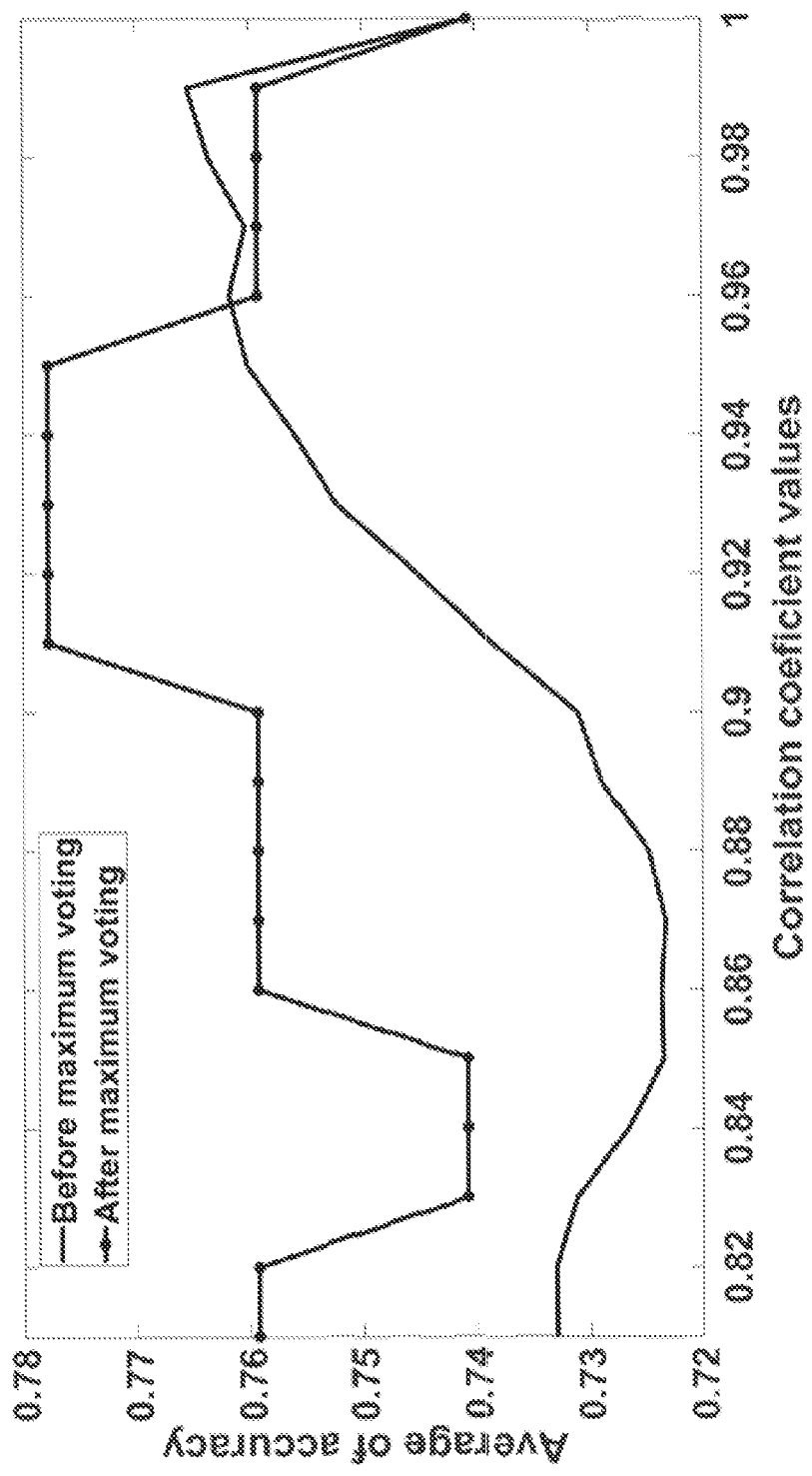
FIG. 6 illustrates an effect of maximum voting, according to one embodiment of the present invention.

In one embodiment, the prediction model can determine risk scores for the middle slice and each of the adjacent slices. In one embodiment, the final ultrasound-based risk score for the renal system can be the maximum risk score from among the middle slice and the adjacent slices. FIG. 6 is a graph of average accuracy of a risk score according to an example embodiment of the present invention. Using the maximum risk score (maximum voting) can increase the accuracy of the risk score in predicting severe kidney obstruction according to one embodiment of the present invention. FIG. 6 also illustrates a relationship between the correlation coefficient and the accuracy of the risk score. According to one implementation of the prediction model, a maximum accuracy can be achieved based on a correlation coefficient of the adjacent slices, e.g., a correlation coefficient of at least 0.83.

In one embodiment, the final ultrasound-based risk score can be a weighted score based on the individual risk scores of the middle slice and the adjacent slices. FIG. 7 is a flow chart of a method 700 for predicting an obstruction severity level using weighted voting of risk scores according to one embodiment of the present invention. The prediction model can generate a risk score for each slice in step 710. In one embodiment, a weight for the risk score of each slice can be determined using the difference (r) between the slice and the middle slice. As an illustrative example, the slices can be ranked according to their correlation with the middle slice as quantified, for example, by the Pearson correlation coefficient. The difference (r) between a slice and the middle slice can be a function of the ranking of the slice. For example, the difference (r) can be the distance between the slice and the middle slice when ranked. In one embodiment, the weight can be calculated using a function, e.g., a multiquadric radial basis function. For example, a function $\phi_{(r)}$=sqrt $(1+(\epsilon r)^2)$ can be applied to calculate the weight $\phi_{(r)}$ for each slice as a function of the difference (r). $\epsilon$ is a scale parameter and can be used to tune the shape of the function. In a non-limiting example, the scale parameter for the multiquadric function $\epsilon$ can be, e.g., 1e−3 and the threshold for a final risk score that corresponds to critical obstruction can be, e.g., 0.9.

In one embodiment, the risk score for each slice can be multiplied by the weight $\phi_{(r)}$ for the slice to determine a weighted risk score. In one embodiment, the weighted risk scores for the middle slices and the adjacent slices can be added to determine the final ultrasound-based risk score in step 730. In one embodiment, a sum-score fusion technique, a median-score fusion, and/or a product-score fusion technique can be used to determine a final ultrasound-based risk score. In one embodiment, the risk scores can be normalized before or after fusion. In one embodiment, the risk scores can be fused using at least one neural network (e.g., at least one convolutional neural network with or without at least one fully connected network).

In one embodiment, a Heaviside step function (a unit step function) can be used to assess a final ultrasound-based risk score using a threshold. In one embodiment, the argument of the Heaviside step function can be $$\frac{\sum_{i=1}^{N} p_i * \emptyset(r_i)}{\sum_{i=1}^{N} \emptyset(r_i)} - Thr$$

wherein $p_i$ is the risk score for each ultrasound image slice, $\emptyset(r_i)$ is the weight for the ultrasound image slice, and N is the number of selected slices. Thr can be a threshold for a presence or severity of renal obstruction, e.g., 0.9. In one embodiment, the threshold for renal obstruction can be learned. In one embodiment, the output of the Heaviside step function, $$Unit\left(\frac{\sum_{i=1}^{N} p_i * \emptyset(r_i)}{\sum_{i=1}^{N} \emptyset(r_i)} - Thr\right),$$

can be a predictive score based on the ultrasound images. In an example embodiment, the output of the Heaviside step function can be 0 if the argument is less than or equal to 0 and 1 if the argument is greater than 0. The final ultrasound-based risk score can thus be a predictor of a presence and/or severity renal obstruction. In one embodiment, the final ultrasound-based risk score can be a predictor of a presence or absence of renal obstruction meeting a certain threshold, e.g., a metric of renal function. In one embodiment, the final ultrasound-based risk score can be evaluated by a classifier, the classifier including, but not limited to, a logistic regression classifier, a linear classifier, a binomial classifier, a polynomial classifier, a quadratic classifier, a pure quadratic classifier, a support vector machine, a perceptron, a random forest, a Naïve Bayes classifier, a decision tree, a K-nearest neighbor classifier, a neural network, or a deep learning-based model.

In one embodiment, clinical patient information can be used to determine a final risk score after the final ultrasound-based risk score has been determined, as in step 740. In one embodiment, clinical patient information can be used as inputs to a neural network to determine the final risk score given the final ultrasound-based risk score. The neural network can include a convolutional neural network and/or at least one fully connected network. Clinical patient information can include, but is not limited to, demographic information, race/ethnicity, age, sex, height, weight, infection status, presence of fever, urinary tract infection status, circumcision status, image side, hydroureter status, ureterocele status, congenital/antenatal/prenatal hydronephrosis, sacral agenesis, presence of stones, neuropathic bladder, pelvic kidney, Dietl's crisis, solitary, multi-cystic, or dysplastic kidney, duplication, posterior urethral valve, chronic kidney disease, mast cells, inflammatory kidney disease, prune belly, congenital anomalies, vesicoureteral reflux, abdominal pain, and/or renal failure. In one embodiment, the clinical patient information can also include SFU grades of the ultrasound images. In one embodiment, the clinical patient information can include information about the dilation size of the collecting system. For example, a number of adjacent slices used to assess obstruction can be used as an indicator of dilation size of the collecting system, especially for severe hydronephrosis cases. The number of adjacent slices and/or alternate indicators of dilation size can also be used to determine the final risk score. The clinical patient information can be used to further categorize, define, or assess the final risk score.

The final risk score is outputted in step 750 based on the final ultrasound-based risk score and the clinical patient information. In one embodiment, the final risk score can be a maximum, mean, median, product, fusion, or weighted voting of at least one risk score. The at least one risk score can include the final ultrasound-based risk score and risk scores related to the clinical patient information. In one embodiment, a predictive model of final risk score can be used to assess the final risk score. According to one embodiment, the predictive model of final risk score can be evaluated by a classifier, including, but not limited to, a logistic regression classifier, a linear classifier, a binomial classifier, a polynomial classifier, a quadratic classifier, a pure quadratic classifier, a support vector machine, a perceptron, a random forest, a Naïve Bayes classifier, a decision tree, a K-nearest neighbor classifier, a neural network, or a deep learning-based model.

In one embodiment, a threshold can be used to assess the final risk score. The final risk score can be a prediction of obstruction severity or appearance. In one embodiment, obstruction severity can be defined according to a TMA value. For example, the final risk score can be a probability of the kidney function being characterized by a T½ value greater than a threshold value of 20 minutes, e.g., 30 minutes, 40 minutes. A T½ value of at least 20 minutes can be considered a clinical indicator of critical ureteropelvic junction obstruction, which is indicative of severe hydronephrosis. In another embodiment, the final risk score can be used to predict obstruction severity according to kidney drainage, e.g., clearance after 30 minutes (C30), upright clearance (CUP) as a percentage of residual tracer cleared in the upright position. In another embodiment, the final risk score can be used to predict a measure of differential renal function. In another embodiment, the final risk score can be used to predict a need for medical attention, including, but not limited to, surgery, discharge from a hospital or similar clinical setting, and longitudinal follow-up recommendations.

Figure 8:
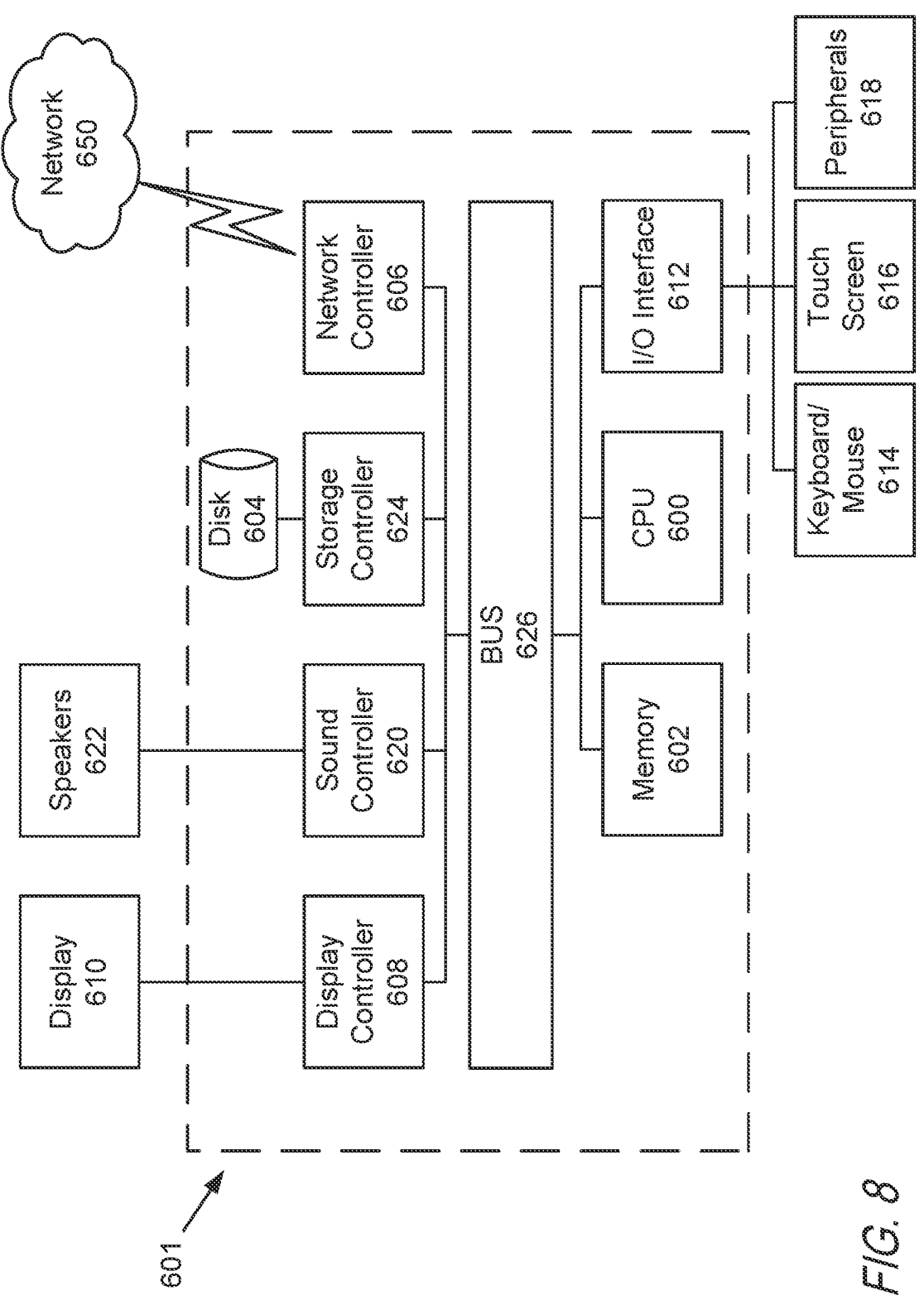
FIG. 8 is a schematic of a hardware configuration of a device for performing a method, according to an exemplary embodiment of the present disclosure.

In one embodiment, the image standardization and hydronephrosis severity and appearance prediction model can be implemented by a computing device or system, such as the device or system as illustrated in FIG. 8. In one embodiment, the computing device can be connected to an ultrasound machine. Next, a hardware description of a device 601 according to exemplary embodiments is described with reference to FIG. 8. In FIG. 8, the device 601 includes processing circuitry, as discussed above. The processing circuitry includes one or more of the elements discussed next with reference to FIG. 8. In FIG. 8, the device 601 includes a CPU 600 which performs the processes described above/below. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device 601 communicates, such as a server or computer.

Further, the claimed advancements may be provided as a utility application, background daemon, or component of an operating system, or combination thereof, executing in conjunction with CPU 600 and an operating system such as Microsoft Windows, UNIX, Solaris, LINUX, Apple MAC-OS and other systems known to those skilled in the art.

The hardware elements in order to achieve the device 601 may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the processes described above.

The device 601 in FIG. 8 can also include a network controller 606, such as an Intel Ethernet PRO network interface card from Intel Corporation of America, for interfacing with network 650, and to communicate with the other devices. As can be appreciated, the network 650 can be a public network, such as the Internet, or a private network such as an LAN or WAN network, or any combination thereof and can also include PSTN or ISDN sub-networks. The network 650 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The device 601 further includes a display controller 608, such as a NVIDIA GeForce GTX or Quadro graphics adaptor from NVIDIA Corporation of America for interfacing with display 610, such as an LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners.

A sound controller 620 is also provided in the device 601 to interface with speakers/microphone 622 thereby providing sounds and/or music. In one embodiment, the device 601 can include a data acquisition (DAQ) controller to receive data corresponding to the ultrasound images.

The general purpose storage controller 624 connects the storage medium disk 604 with communication bus 626, which may be an ISA, EISA, VESA, PCI, or similar, for interconnecting all of the components of the device 601. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

The invention claimed is:

1. A method for predicting a severity and appearance of renal obstruction, the method comprising:
   receiving, via processing circuitry, a plurality of medical images corresponding to a kidney of a patient;
   identifying, via the processing circuitry, the kidney in the plurality of medical images;
   selecting, via the processing circuitry, at least one relevant image from the plurality of medical images, the at least one relevant image being selected based on a relationship to renal function;
   standardizing, via the processing circuitry, the at least one relevant image;
   determining, via a deep learning model executed by the processing circuitry, at least one risk score based on the at least one relevant image; and
   determining, via the processing circuitry, a final ultrasound-based risk score based on the at least one risk score, wherein the final ultrasound-based risk score is an indication of a presence of renal obstruction and/or a probability of renal obstruction.

2. The method of claim 1, wherein identifying the kidney in the plurality of medical images includes segmenting the kidney or localizing a boundary of the kidney.

3. The method of claim 1, wherein standardizing the at least one relevant image includes standardizing a field of view, an intensity, and/or a size of the at least one relevant image.

4. The method of claim 3, wherein standardizing the field of view includes standardizing an orientation of the kidney in the at least one relevant image along a longest axis of the kidney in a coronal view.

5. The method of claim 1, wherein the at least one relevant image includes a middle slice image.

6. The method of claim 5, wherein the at least one relevant image further includes at least one adjacent slice image, and wherein the at least one adjacent slice image is selected based on a correlation between the at least one adjacent slice image and the middle slice image.

7. The method of claim 1, wherein the final ultrasound-based risk score is a maximum, a product, or a median of the at least one risk score, or wherein the final ultrasound-based risk score is determined via at least one neural network.

8. The method of claim 1, wherein the final ultrasound-based risk score is a weighted fusion of the at least one risk score and wherein a weight of the at least one risk score is based on a difference between the at least one relevant image and a middle slice image, wherein the difference is based on correlation analysis or a deep learning-based approach.

9. The method of claim 1, further comprising determining, via the processing circuitry, a final risk score based on the final ultrasound-based risk score and clinical patient information, wherein the final risk score is a label of a presence of renal obstruction and/or a probability of renal obstruction.

10. The method of claim 9, wherein the final risk score is determined using a neural network.

11. An apparatus for predicting a severity and appearance of renal obstruction, comprising:

processing circuitry configured to:

receive a plurality of medical images corresponding to a kidney of a patient;

identify the kidney in the plurality of medical images;

select at least one relevant image from the plurality of medical images, the at least one relevant image being selected based on a relationship to renal function;

standardize the at least one relevant image;

determine, via a deep learning model, at least one risk score based on the at least one relevant image; and determine a final ultrasound-based risk score based on the at least one risk score, wherein the final ultrasound-based risk score is an indication of a presence of renal obstruction and/or a probability of renal obstruction.

12. The apparatus of claim 11, wherein the processing circuitry is further configured to segment the kidney or localize a boundary of the kidney to identify the kidney in the plurality of medical images.

13. The apparatus of claim 11, wherein the processing circuitry is configured to standardize a field of view, an intensity, and/or a size of the at least one relevant image.

14. The apparatus of claim 13, wherein the processing circuitry is configured to standardize an orientation of the kidney in the at least one relevant image along a longest axis of the kidney in a coronal view to standardize the field of view.

15. The apparatus of claim 11, wherein the at least one relevant image includes a middle slice image.

16. The apparatus of claim 15, wherein the at least one relevant image includes at least one adjacent slice image and wherein the processing circuitry is configured to select the at least one adjacent slice image based on a correlation between the at least one adjacent slice image and the middle slice image.

17. The apparatus of claim 11, wherein the final ultrasound-based risk score is a weighted fusion of the at least one risk score and wherein a weight of the at least one risk score is based on a difference between the at least one relevant image and a middle slice image, wherein the difference is based on correlation analysis or a deep learning-based approach.

18. The apparatus of claim 11, wherein the processing circuitry is further configured to determine a final risk score based on the final ultrasound-based risk score and clinical patient information, wherein the final risk score is a label of a presence of renal obstruction and/or a probability of renal obstruction.

19. The apparatus of claim 18, wherein the final risk score is determined using a neural network.

20. A non-transitory computer-readable storage medium for storing computer-readable instructions that, when executed by a computer, cause the computer to perform a method for predicting a severity and appearance of renal obstruction, the method comprising:

receiving, via processing circuitry, a plurality of medical images corresponding to a kidney of a patient;

identifying, via the processing circuitry, the kidney in the plurality of medical images;

selecting, via the processing circuitry, at least one relevant image from the plurality of medical images, the at least one relevant image being selected based on a relationship to renal function;

standardizing, via the processing circuitry, the at least one relevant image;

determining, via a deep learning model executed by the processing circuitry, at least one risk score based on the at least one relevant image; and determining, via the processing circuitry, a final ultrasound-based risk score based on the at least one risk score, wherein the final ultrasound-based risk score is an indication of a presence of renal obstruction and/or a probability of renal obstruction.

* * * * *